United States Patent [19]

Kulli

[11] Patent Number: 4,900,307
[45] Date of Patent: * Feb. 13, 1990

[54] SAFETY RETRACTING NEEDLE FOR USE WITH SYRINGE

[76] Inventor: John C. Kulli, 1920 Spruce St., South Pasadena, Calif. 91030

[*] Notice: The portion of the term of this patent subsequent to May 31, 2005 has been disclaimed.

[21] Appl. No.: 200,636

[22] Filed: May 31, 1988

Related U.S. Application Data

[63] Continuation-in-part of Ser. No. 43,691, Apr. 29, 1987, Pat. No. 4,747,831.

[51] Int. Cl.$^4$ .............................................. A61M 5/24
[52] U.S. Cl. .................................. 604/110; 604/198; 604/218
[58] Field of Search ............... 604/110, 197, 198, 192, 604/194, 136, 138, 162, 263, 278

[56] References Cited

U.S. PATENT DOCUMENTS

| | | | |
|---|---|---|---|
| 2,876,770 | 3/1959 | White | 604/198 |
| 3,314,428 | 4/1967 | Johnson et al. | 604/192 |
| 3,890,971 | 6/1975 | Leeson et al. | 604/110 |
| 4,542,749 | 9/1985 | Caselgrandi | 128/752 |
| 4,664,654 | 5/1987 | Strauss | 604/198 |

Primary Examiner—Stephen C. Pellegrino
Attorney, Agent, or Firm—Peter I. Lippman

[57] ABSTRACT

A hollow needle projects from the "forward" end of a hollow handle. A syringe communicates with the interior of the needle by way of the hollow handle. After use for passing liquid between the syringe and a patient's body, the needle is released from the handle and its sharp end retracted into the handle, beyond reach. The handle has an aperture big enough for the needle but not for fingertips. The needle rides in a carrier block that slides inside the handle. Initially the block is secured in the handle against the forward end, with the sharp end of the needle protruding out through the aperture. A manually releasable latch holds the block in this position. The latch includes mutually interfering stop elements on the exterior of the block and interior of the handle. After liquid is injected into or withdrawn from the patient's body, the person using the device withdraws the needle from the patient and manually triggers the carrier-block latch by squeezing or rotating one stop element out of engagement with the other. Then a coiled spring drives the block rearward to retract the needle into the handle. At the rear of the handle a stop halts the block and needle to safely confine them within the handle. A standard-size fitting on the rear of the handle permits liquid flow between the patient and a standard syringe with a standard front fitting.

44 Claims, 2 Drawing Sheets

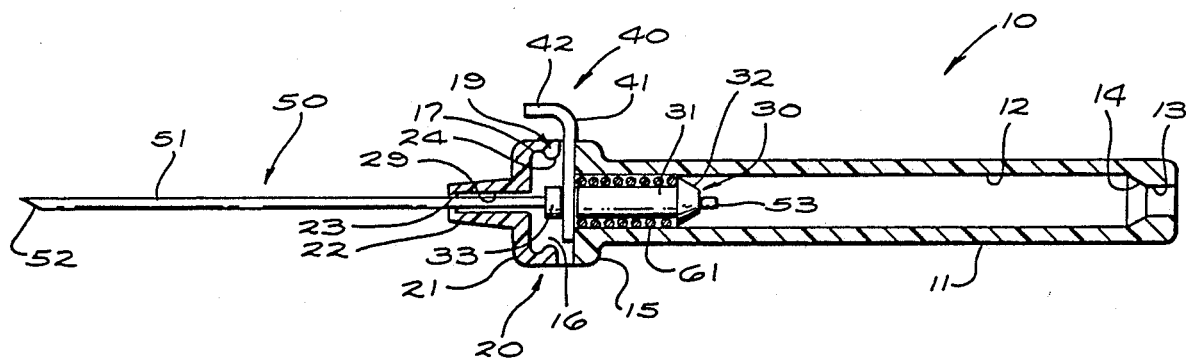
FIG. 1
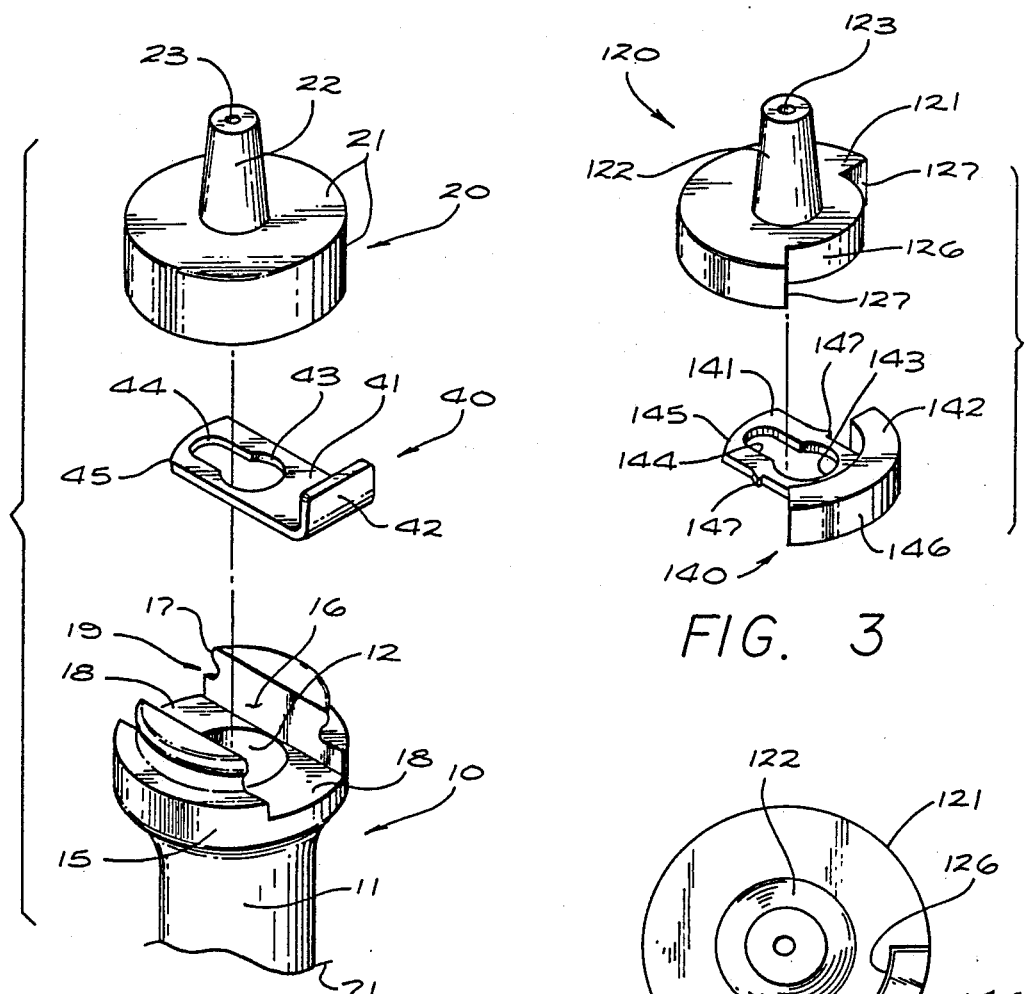
FIG. 2
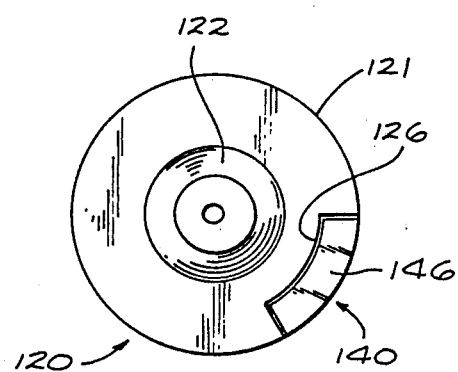
FIG. 3
FIG. 3a

SAFETY RETRACTING NEEDLE FOR USE WITH SYRINGE

RELATED APPLICATION

This is a continuation-in-part of my copending U.S. patent application 7/043,691, filed Apr. 29, 1987, and issuing on May 31, 1988, as U.S. Pat. No. 4,747,831.

BACKGROUND

1. FIELD OF THE INVENTION

This invention relates generally to medical appliances; and more particularly to devices such as syringes for withdrawing liquids from or injecting liquids into a patient's body.

2. PRIOR ART

My above-mentioned copending application and patent, whose disclosures and other recitations are hereby fully incorporated by reference herein, set forth in detail that a severe problem has developed in relation to all devices for withdrawing blood and other liquids from patients.

That problem relates to transmission of fatal and currently incurable diseases by exchange of body substances between people—and particularly transmission of such diseases to medical personnel who inadvertently touch needle tips after withdrawal from infected patients. The same problem is present with respect to devices for injecting liquids or other substances into patients.

The above-mentioned application and patent also discuss in detail numerous prior-art devices relating to guarding of needle tips. Such devices include a hypodermic needle commercially available from the firm ICU Medical, Inc., under the trade name "ICU High Risk Needle," as well as those disclosed and claimed in U.S. Pat. Nos. 4,592,744, 4,026,287, 4,631,057, 4,643,199, 4,573,976, 4,643,200, 4,425,120, 3,890,971, 2,876,770, 2,674,246 and 3,134,380.

My above-mentioned application and patent also disclose and claim my invention for use in guiding a cannula into place in a patient's body, to facilitate attachment of an intravenous tube for various well-known medical purposes. That invention is a safety device which thereafter protects medical personnel, trash-handling personnel and others from contact with portions of the device that have been within the patient.

I consider that invention to be an important advance in the field of medical safety. As disclosed in my above-mentioned application and patent, however, that invention left unresolved the related problem of infection by contact with syringe needles.

SUMMARY OF THE DISCLOSURE

As stated, the invention disclosed in my patent identified above was intended for use with cannulas. I have realized, however, that most or all of the embodiments of that invention are amenable, with certain modifications—and in some cases even without modification—to use with a syringe for injection or withdrawal of liquids. More specifically: the embodiments previously disclosed include a needle mounted for retraction in a hollow handle, and the handle preferably has a standard fitting for use in attaching a standard intravenous tube. That same fitting (or if preferred a differently configured fitting) can be used in attachment of a standard syringe tip (or if preferred a nonstandard syringe tip). Liquid can then be passed between a patient and a standard syringe or nonstandard syringe, by way of the needle and the hollow handle. In view of this realization I have further noted that other means may be employed, if desired, for communication between a syringe and the needle. That is to say, the hollow handle itself is preferably but not necessarily part of the fluid path.

From the foregoing informal introduction I shall now proceed to a more rigorous summary of the disclosure of my present invention.

My invention is a safety device for use with a syringe in injecting a substance into a patient or withdrawing a substance from a patient. It also serves thereafter to protect medical personnel, trash-handling personnel, and any other people who may have casual contact with the device after its use. The device protects all such individuals from contact with portions of the device that have been within the patient.

The device of my present invention includes a needle for piercing the patient, and for guiding and carrying such substance into or out from the patient. The needle has a hollow shaft with at least one sharp end.

My invention also has a hollow handle that is adapted to enclose at least the sharp end of the needle. The handle is particularly adapted to so enclose the sharp beyond reach of such people's fingers.

The invention also has some means for establishing communication between the syringe and the hollow needle—for passage of the substance between the syringe and the needle. For purposes of generality in expression I shall refer to these means as the "communication-establishing means."

In addition the invention includes some means for securing the shaft of the needle to the handle, with the sharp end projecting from the handle. Again for purposes of generality, I shall refer to these as the "securing means."

My invention further requires some means for releasing the securing means—and for retracting the sharp end of the needle into the handle. These means, again, I shall term the "releasing and retracting means." Retraction of the needle by these means is substantially permanent.

The releasing and retracting means of my invention are manually actuable by a simple unitary motion. By "simple unitary" motion I mean a motion that is not compound, one that entails a single-stage movement in just one direction.

The amplitude of this motion is substantially shorter than the length of the needle. Alternatively, it may be described as small compared with the size of the user's fingers, or hand generally.

Possibly the foregoing may be a discussion of my invention in its most general form. As will be appreciated, however, there are additional features which I prefer to incorporate in my invention to particularly optimize its efficacy.

For example, I prefer that the communication-establishing means include some means for connecting the syringe to the hollow handle; and that the hollow needle have another end that is in communication with the interior of the hollow handle. In this preferable form of the invention, passage of the substance between the syringe and the needle is by way of the hollow handle.

As another and more specific example, I prefer that the syringe be a separate article or product, and that it have a standard-size front fitting for passage of liquids between the separate syringe and the patient's body.

Here the communication-establishing means comprise a standard-size rear fitting on the hollow handle for attachment of the separate syringe.

In this example too, once again the hollow needle has another end in communication with the interior of the handle. Thus passage of the substance between the separate syringe and the patient's body is by way of the rear fitting and the hollow handle, as well as the needle.

Other desirable and preferred features include some means for deterring leakage of the substance from the safety device. In the natural uses of my cannula insertion-set invention, liquid pressures are relatively low, but in use of a syringe somewhat higher pressures can be developed.

Accordingly it is desirable to give some attention to preventing leakage of substances being conveyed between the patient and the syringe. I have also discovered that it is sometimes desirable to deter leakage of such substances that may trickle from the rear fitting of the hollow handle after conveyance of substances to or from the body is completed.

Leakage-deterring means advantageously include a sealing material applied to moving parts of the releasing and retracting means. Such a sealant blocks any liquid-escape path along such parts.

Other leakage-deterring means advantageously include an absorbent mass—such as a small fibrous mat or sponge—disposed within the hollow handle. Such an absorber may be most useful in absorbing liquid near the rear fitting of the hollow handle after the syringe is removed from that fitting.

Still other advantageous features include an aperture, defined in the handle, that is small compared with the fingers of such people to be protected—but large enough for passage of the needle. Another preferred feature is a trigger mechanism, forming part of the releasing and retracting means, which is operable from outside the handle.

The releasing and retracting means also preferably include some means—such as, for example, a coil spring—for positively biasing the sharp end of the needle toward retraction into the handle. After retraction has actually occurred, these biasing means preferably continue to operate, to retain the sharp end of the needle retracted within the handle.

My invention preferably includes a block that is fixed to and extending from the needle, and that forms a part of the securing means. The block is adapted to be restrained within the handle, with the sharp end of the needle projecting from the handle.

The block, when present, is also responsive to the releasing and retracting means, to withdraw the needle into the handle. The releasing and retracting means are preferably actuable by just one hand of a user of the device. It is also strongly preferable that a user can actuate these means without looking at the device during the actuation.

More specifically, I prefer to provide stop elements respectively defined within the handle and on the block. These elements engage each other to restrain the block from retracting the needle.

I also prefer to provide a trigger mechanism, including a manually operable release member. The trigger mechanism disengages the stop elements from one another to release the block and thereby retract the needle.

As previously mentioned, my device is for use with a syringe. The syringe communicates with the needle as already described.

Thus the syringe may be regarded as a part of the environment of my invention. For some purposes, however, to the extent indicated in the appended claims, it is appropriate to regard the syringe as a part of the invention itself.

All of the foregoing operational principles and advantages of the present invention will be more fully appreciated upon consideration of the following detailed description, with reference to the appended drawings, of which:

BRIEF DESCRIPTION OF THE DRAWINGS

FIG. 1 is a side elevation, mostly in longitudinal section, of a preferred embodiment of my invention, shown with the needle secured in extended position for carrying a substance between the patient and a syringe.

FIG. 2 is an enlarged and exploded perspective drawing, drawn interrupted at one end, of some of the parts of the FIG. 1 embodiment.

FIG. 3 is a similar view of a variant form of some of the FIG. 2 parts.

FIG. 3a is a somewhat schematic end elevation of the FIG. 3 parts assembled.

DETAILED DESCRIPTION OF THE PREFERRED EMBODIMENTS

Figure 4:
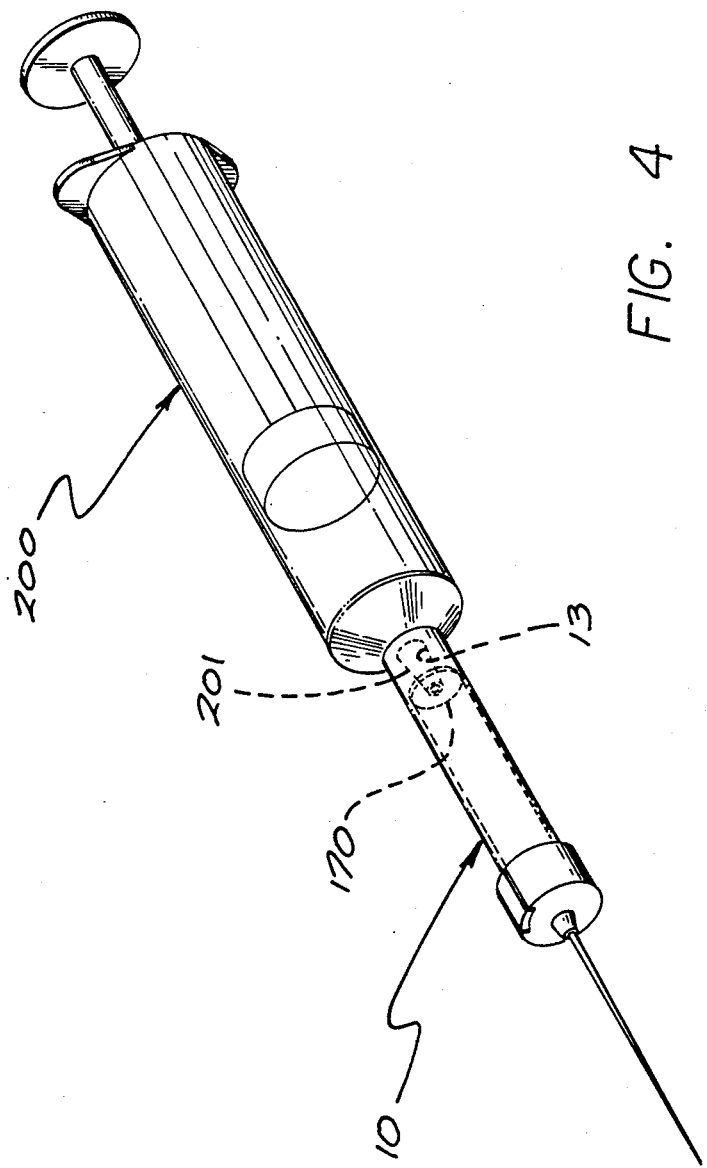
FIG. 4 shows the same embodiment with a generally conventional or standard syringe attached.

As shown in FIGS. 1 and 2, an embodiment of my invention which I now prefer includes a shaped hollow handle 10. This embodiment also includes a nosepiece 20 that is securely fixed to a forward end of the handle 10, and a carrier block 30 that is slidably disposed within the handle 10.

The embodiment of FIGS. 1 and 2 also includes a latch 40 that secures the carrier block 30 near the forward end of the handle, close to the nosepiece 20; and a needle 50 that is carried by the block 30 and extends from the handle 10 through the nosepiece 20. Finally, this embodiment includes a spring 60 that is positioned within the handle 10 and encircles part of the carrier block.

The various parts of this embodiment of my invention are particularly configured for ease and economy in manufacture. Accordingly in the description of this embodiment I shall mention many details of configuration. I mean it to be understood that all such details are included to enable a person skilled in the art to practice my invention in its best mode as currently envisioned, and in particular very cost-effectively.

The handle 10 is preferably but not necessarily injection molded from plastic such as polycarbonate. It includes a long, generally right-circularly cylindrical outer grip surface 11, radially enlarged near its forward end to form a thumb stop 15.

The thumb stop, in turn, is the rearward part of a latch-housing portion 15–19—better seen in FIG. 2. The thumb stop 15 is a right-circular cylinder, much shorter than but conaxial with the outer grip surface 11.

The remainder of the latch-housing portion 15–19 is also circularly symmetrical, except that it is bisected at its forward end by a broad transverse latch-guide slot 16, 18. The transverse latch-guide slot 16, 18 has a bottom surface 18 and two opposed side walls 16.

As viewed from the end of the device, each side wall 16 of the latch-guide slot 16, 18 is formed along a chord of the circular shape of the thumb stop 15. Thus in effect the latch-guide slot 16, 18 divides the forward portion of the latch housing 15-19 into two identical upstanding pillars as seen clearly in FIG. 2. Each pillar is formed as a segment on the chord.

A circumferential groove 19, also better seen in FIG. 2, is formed near the forward end of the latch housing 15-19. This groove 19 is spaced away from the bottom surface 18 of the latch-guide slot 16, 18. At the very end of the latch housing there is a flange 17, of diameter smaller than that of the thumb stop 15.

I prefer to form neither the groove 19 nor the flange 17 as rectangular in longitudinal section. Rather, to facilitate removal from an injection mold—and also to ease snap-together assembly with the nosepiece 20—I prefer to form the groove 19 and the flange 17 as arcs in longitudinal section.

A centered longitudinal bore 12 is formed within the handle 10, exposed at the bottom surface 18 of the latch-guide slot 16, 18. This bore is very generally right-circularly cylindrical, but preferably has a very slight taper or draft widening toward the rear end of the handle to facilitate removal of the handle from a mold.

Near the rear end of the bore 12, however, there formed an internally frustoconical stop surface 14—narrowing the bore 12 slightly. At the extreme end of the bore 12 is a short end section 13, opening at the rear end of the handle 10.

The end section 13 of the bore is preferably slightly tapered outward toward the rear, and (notwithstanding the drawing) of the same length and taper as the needle guide 22. The taper of the frustoconical stop surface 14 is slight, and the overall diametral inset from the long section 12 of the bore to the end section 13 of the bore is very slight.

By virtue of these details of configuration, the handle can be popped out of an injection or other mold by means of a slight deformation (expansion) of the rear end. That is, a separate core piece in the mold is not needed.

The nosepiece 20 is a right-circularly symmetrical article with two main sections: a relatively slender forward needle guide 22 and a radially enlarged rearward canopy 21. The needle guide 22 has a central bore that is somewhat larger than the diameter of the needle 50. At the extreme tip of the needle guide 22 this central bore narrows to a fine aperture 23. The diameter of the end aperture 23 is chosen as a tradeoff between (1) complete stabilization of the needle and (2) minimum friction in sliding clearance between the guide 22 and needle.

The canopy 21 has a right-circularly cylindrical outer surface, preferably matching the outer surface of the thumb stop 15. Formed in the rear end of the canopy is a cavity, internally shaped to mate securely with the contours of the latch housing 15-19.

More particularly, at the very end of the cavity there is an inward flange or lip 24 (FIG. 1) that accurately fits into and engages the groove 19 of the latch housing 15-19. Due to the previously mentioned spacing of the groove 19 away from the bottom surface 18 of the latch-guide slot 18, the inward lip 24 of the nosepiece 20 is similarly spaced from the bottom surface 18. The resulting gap between the lip 24 and the surface 18 defines a track for operation of the latch 40.

The nosepiece can be made of the plastic available commercially under the trade name "Delrin." That material is selected primarily because it is relatively easy to form.

The carrier block 30 has a very narrow central bore in which the needle 50 is tightly gripped. The block 30, also of Delrin, may be press-fit, shrink-fit, and/or cemented on the needle, or molded in place.

The outside of the carrier block 30 is circularly symmetrical. It has an extended barrel 31 that may be right-circularly cylindrical. At the rear end of the barrel 31 is a frustoconical stop section 32 whose forward end is radially enlarged relative to the barrel 31. The stop section tapers inward toward the extreme rear of the block 30.

The rear, frustoconical surface of the stop section 32 is shaped to seat against the previously mentioned internal frustoconical stop section 13 of the handle 10, when the needle is fully retracted. The front end of the stop section 32 forms a generally planar, annular, step radially outward from the barrel 31, for purposes to be seen shortly.

The forward end section 33 of the block 30 is of the same diameter as the barrel section 31. Between the forward end section 33 and the barrel 31, however, there is formed a circumferential latch groove. Thus the forward end section 33 forms a flange adjacent to and just forward from the latch groove.

The latch 40 has a flat slide section 41, and at one end of the slide a short pushbutton section 42 bent or formed at right angles to the slide 41. A keyhole-shaped cutout 43, 44, is defined in the slide.

The enlarged portion 43 of this cutout is nearer to the pushbutton 42. The end 45 of the slide 41 opposite the pushbutton 42 lies immediately past the narrowed portion 44 of the cutout 43, 44. The latch can be made from a suitably selected 300 series stainless steel.

The needle 50, with its shaft 51, sharpened tip 52, and rear end 53, is generally conventional—and also of stainless steel. It is longer than usual, to allow for the extra length required to pass into and through the carrier block 30. The block 30 is fixed upon the needle shaft 51 very near the rear end 53 of the needle.

Finally, the preferred embodiment of FIGS. 1 and 2 includes a coil spring 62, sized to encircle the outside diameter of the carrier-block barrel 31. The spring should be long enough to hold the mechanism fully retracted. The minimum diameter of the handle bore 12 is selected to just enclose the spring 61—without significantly restricting the free expansion of the spring.

To assemble the device, the carrier block 30 is first fixed to the needle 50 as previously described. Then the needle 50 is inserted through the spring 61, until the carrier block 30 reaches the spring. This same general motion is then continued, to insert the flange 33 and barrel 31 of the carrier block through the spring 61.

The result of this procedure is that one end of the spring is seated against the previously mentioned step that is located at the rear end of the carrier-block barrel 31.

Next the needle is inserted into the keyhole cutout 43, 44 in the slide 41, until the carrier block 30 reaches the slide 41. The same general motion is continued, passing the flange 33 at the forward end of the carrier block through the enlarged section 43 of the keyhole cutout 43, 44 in the slide 41. The result of this procedure is to align the slide 41 longitudinally with the circumferential groove (between the barrel 31 and flange 33) in the carrier block 30. Next the slide 41 is moved laterally toward the pushbutton 42 so that the narrower portion 44 of the keyhole cutout 43, 44 is captured in the circumferential groove in the block 30.

The carrier block 30, with the needle 50, spring 60 and latch 40 in effect threaded upon it as just described, is then inserted rear-end-first into the front end of the bore 12 in the handle 10.

The slide 41 thus fits between the two side walls 16 of the latch-guide slot 16, 18, and rests against the bottom surface 18 of the slot. The needle is then inserted through the bore 29 and clearance aperture 23 in the nosepiece 20; and the shaped forward end 16, 17, 19 of the latch guide is then snapped in place within the canopy 21 of the nosepiece 20.

The handle 10 is now in effect longer, by the added length of the nosepiece 20. When assembled in this way, the slide portion 41 of the latch 40 is positioned in the previously mentioned "track" that is defined between the bottom surface 18 (FIG. 2) of the latch-guide slot 16, 18 and the inner lip 19 (FIG. 1) of the nosepiece 22.

The pushbutton 42 is pulled fully outward radially from the latch-guide housing 15–19 (or, to now put it more completely, 1–21). The needle 50 is now firmly secured in position, extending forward from the effectively lengthened handle.

After the nosepiece 20 is snapped into place on the end of the handle 10, these two parts are preferably secured together as by sonic welding. (If preferred they can be held together by cement, naturally applied before assembly, or by through pins, etc.) This procedure is desirable to ensure permanence of attachment—and thus permanence of capture of the needle after retraction.

My invention makes use of a syringe 200 (FIG. 4) that is preferably but not necessarily an entirely conventional one, either disposable or reusable as appropriate. It has a conventional and in fact industrial-standard attachment or tip 201—for example, any of those commercially manufactured and distributed under the trade name "Luer"—which attaches by press fit or coarse threading action to the rear fitting 13 of my invention.

As can be seen, my invention when used with a syringe introduces a dead space or volume (primarily the interior volume of the hollow handle) not present in most prior-art apparatus for injecting or withdrawing substances. Accordingly this volume of substance will generally be lost from the substance injected or withdrawn. For my preferred embodiment whose dimensions are tabulated below, the lost volume is about 0.06 cubic inch, or roughly one milliliter.

Therefore, as will now be apparent, the invention should not be used as described in this document with liquids that are extraordinarily valuable. The invention remains useful and practical, however, with a very large number of substances—including, for example, penicillin and even (for most cases) blood.

As mentioned earlier, during pressurized operation with a syringe some liquid may tend to leak from the mechanism. Advantageously the present invention includes means for deterring leakage.

The path for such leakage is past the rear frustoconical portion 32 of the carrier 30, through needle chamber formed between the interior barrel wall 12 and the relieved portion 31 of the carrier, and then along the track 16, 18 provided for operation of the latch 40. Any such tendency toward leakage will be minimized by providing a coating of sterile silicone oil or grease (not illustrated) in the area of these moving parts 30, 40.

Another potential annoyance is leakage or splash of residual liquid from the rear of the barrel 12 after use of the device. Such leakage can be minimized by disposing within the barrel 12 a sterile absorbent fibrous pad or sponge 170 (FIG. 4) of a biologically inert material such as Teflon ®.

A generally conventional safety cover for the needle of my invention should be provided, to protect against accidental puncture and against contamination of the needle before use. The cover must be adapted to fit over the pushbutton 42 without triggering it—and preferably also to fit between the pushbutton 42 and the canopy 21, to deter movement of the slide 41 due to vibration in shipment or other handling.

After use, however, the safety cover may be thrown away. In particular, it may be discarded either together with my invention or separately, since the needle is automatically sheathed without that cover.

Dimensions of the rear bore 13 of my preferred embodiment should be the same as the dimensions of standard needle hubs, to mate with standard syringes. For compatibility with one set of commercial standard mating parts, the bore should be roughly 0.275 inch long, and taper from 0.15 inch at the front to 0.20 inch at the rear.

Other dimensions of my preferred embodiment of FIGS. 1 are roughly (in inches):

3.5: length from rear end of handle to forward surface of canopy
2.3: length from forward surface of canopy to tip of needle
0.500: outside diameter of nosepiece canopy
0.350: outside diameter of handle grip surface
0.165: inside diameter of handle bore near trigger
0.170: inside diameter of handle bore near rear end
0.625: length of carrier block
0.165: outside diameter of carrier-block stop section
0.120: outside diameter of carrier-block barrel.

I have described the present invention in detail with respect to just one preferred embodiment. As will be understood, however, most of the embodiments of my above-mentioned cannula-insertion invention, as well as other mechanical configurations, are usable as described herein.

Although I consider the embodiment described above highly desirable, various features could in principle be omitted and the device still correspond to my invention as most broadly envisioned. For example, a tension spring (rather than a compression spring as shown) could be secured to a small hole or hook near the rear end of the needle, to pull the needle into a closed handle without the intermediary of a carrier block.

Alternatively the spring could be omitted, and the needle arranged to fall into the handle under the influence of gravity when a latch is released. Moreover it is not necessary that the rear end of the needle initially be within the handle. Some other element of the apparatus could instead pull the rear end of the needle into the handle when a latch is released.

On the other hand, it is not necessary that after actuation of the latch the rear end of the needle come to rest within the handle: in principle the "back" of the needle could protrude from the rear end of the handle. In this case proper provision must be made, however, to prevent the needle from being accidentally re-extended forward through the nosepiece.

I have had a working model of the FIGS. 1 and 2 embodiment constructed, and I have found its operation excellent. That embodiment, however, may be subject to improvement.

For example, I believe that the variant that is illustrated in FIGS. 3 and 3a may be preferable, though I have not constructed a working model for direct comparison. In FIGS. 3 and 3a the pushbutton is a formed annular-segment plastic piece 142, with an antislip peripheral surface 146; and the nosepiece has a section 126, 127 cut out to accommodate the pushbutton 146.

This configuration seems probably preferable, for ease of operation. The fingers of a person using the device will normally be kept behind the thumb stop 15 (FIGS. 1 and 2), and therefore are unlikely to accidentally operate the button 146.

Even in event of such an accident, there is no harm to the patient or medical personnel. The main adverse result is economic: another insertion set must be obtained. Regular users of the device will quickly learn to avoid inadvertent triggering of the latch.

Another refinement shown in FIG. 3 is that ratchet-shaped detents 147 are provided on the edges of the slide, to interact with corresponding features (not illustrated) formed in the side walls 16 of the guide slot 16, 18. These detents 147 will prevent the trigger from being reset, and thereby discourage attempts to reuse the needle.

I shall now mention still another desirable characteristic of my preferred embodiment, perhaps not clearly illustrated. I prefer to slightly increase the diameter of the large end of the frustoconical stop section 32 of the carrier block, so that it provides a fluid seal against the inside bore 12 of the handle 10—when the trigger is not actuated.

This arrangement facilitates effective fluid communication through the hollow needle by minimizing reliance on maintenance of sanitation at the many intricate surfaces of the spring, internal cavities, etc., that are forward of the stop section 32.

Various features or elements appear in FIGS. 3 and 3a that have not been specifically identified above. Those features or elements are substantially identical to the items in FIGS. 1 and 2 that have corresponding reference numerals—i. e., numerals that differ only by addition of the prefix "1" in FIGS. 3 and 3a.

In principle my invention may be used with either a reusable or a disposable syringe. The syringe, however, of course should be actually reused only when safe and otherwise appropriate. Very generally speaking, syringe reuse with my invention will be safe and appropriate to the extent that syringe reuse with a conventional needle under the same circumstances would be considered safe and appropriate.

It will be understood that the foregoing disclosure is intended to be merely exemplary, and not to limit the scope of the invention—which is to be determined by reference to the appended claims.

I claim:

1. A safety device for use with a syringe in injecting a substance into a patient or withdrawing a substance from a patient and for thereafter protecting people from contact with portions of the device that have been within the patient; said device comprising:
    a needle for piercing such a patient and for carrying such a substance into or out from such a patient, said needle having a hollow shaft with at least one sharp end;
    a hollow handle adapted to enclose at least the sharp end of the needle beyond reach of such people's fingers;
    means for establishing communication between such a syringe and the hollow needle, for passage of such a substance between the syringe and the needle;
    means for securing the shaft to the handle, with the sharp end projecting from the handle; and
    means for releasing the securing means and for substantially permanently retracting the sharp end of the needle into the handle and beyond reach of such people's fingers;
    said releasing and retracting means being manually actuable by a simple unitary motion, of amplitude that is substantially shorter than the shaft of the needle.

2. The safety device of claim 1, wherein:
    the communication-establishing means comprise means for connecting such a syringe to the hollow handle; and
    the hollow needle has another end in communication with the interior of the hollow handle;
    whereby said passage of substance between such a syringe and the needle is by way of the hollow handle.

3. The safety device of claim 2, further comprising:
    means for deterring leakage of such substance from the safety device.

4. The safety device of claim 3 wherein:
    the leakage-deterring means comprise a sealing material applied to moving parts of the releasing and retracting means.

5. The safest device of claim 3, wherein:
    the leakage-deterring means comprise an absorbent mass disposed within the hollow handle.

6. The safety device of claim 2, in further combination with:
    such syringe.

7. The safety device of claim 8, in further combination with:
    such syringe.

8. The safety device of claim 1, for use with such a syringe that is a separate article and that has a standard-size front fitting for passage of liquids between the separate syrnge and the patient's body;
    the communication-establishing means comprise a standard-size rear fitting on the hollow handle for attachment of such separate syringe; and
    the hollow needle has another end in communication with the interior of the hollow handle;
    whereby said passage of substance between the separate syringe and the patient's body is by way of the rear fitting, the hollow handle, and the needle.

9. The safety device of claim 1, in further combination with:
    means for deterring leakage of such substance from the safety device.

10. The safety device of claim 9, wherein:
    the leakage-deterring means comprise a sealing material applied to moving parts of the releasing and retracting means.

11. The safety device of claim 9, wherein:
    the leakage-deterring means comprise an absorbent mass disposed within the hollow handle.

12. The safety device of claim 9, wherein:

the leakage-deterring means comprise a Teflon® sponge disposed within the hollow handle.

13. The safety device of claim 9, wherein the leakage-deterring means comprise:
a sealing material applied to moving parts of the releasing and retracting means; and
an absorbent mass disposed within the hollow handle.

14. The safety device of claim 9, in further combination with:
such syringe.

15. The safety device of claim 1, in further combination with:
such syringe.

16. The safety device of claim 1, wherein:
the handle defines an aperture that is small compared with such people's fingers but large enough for passage of the needle.

17. The safety device of claim 1, wherein the releasing and retracting means comprise:
a trigger mechanism operable from outside the handle.

18. The safety device of claim 1, wherein the releasing and retracting means comprise:
means for positively biasing the sharp end of the needle toward retraction into the handle.

19. The safety device of claim 18, wherein:
the biasing means also operate to retain the sharp end of the needle retracted within the handle.

20. The safety device of claim 1, wherein the securing means comprise:
a block fixed to and extending from the needle, and adapted to be restrained within the handle with the sharp end of the needle projecting from the handle; and adapted for motion within the handle, responsive to the releasing and retracting means, to withdraw the needle into the handle.

21. The safety device of claim 1, wherein:
the releasing and retracting means are actuable by one hand of a user of the device.

22. The safety device of claim 1, wherein:
the releasing and retracting means are manually actuable by a user of the device, employing just one hand and without looking at the device.

23. A safety device for use with a syringe in injecting a substance into a patient or withdrawing a substance from a patient and for thereafter protecting people from contact with portions of the device that have been within the patient; said device comprising:
a hollow needle for piercing such patient and for guiding and carrying such a substance into or out from such a patient, said needle having a hollow shaft with at least one sharp end;
a hollow handle that defines an aperture which is small compared with such people's fingers but large enough for passage of the needle, and that is otherwise adapted to enclose at least the sharp end of the needle;
means for establishing communication between such a syringe and the hollow needle, for passage of such a substance between the syringe and the needle;
a block fixed to and extending from the needle, and restrained within the handle with the sharp end of the needle projecting out of the handle through the aperture, and adapted for motion within the handle to withdraw the needle into the handle; and
a trigger mechanism, actuable from outside the handle for releasing the block, and including positive biasing means for forcibly moving the block within the handle to substantially permanently retract the sharp end of the needle into the handle and beyond reach of such people's fingers.

24. The safety device of claim 23, wherein:
the communication-establishing means comprise means for connecting such a syringe to the hollow handle; and
the hollow needle has another end in communication with the interior of the hollow handle;
whereby said passage of substance between such a syringe and the needle is by way of the hollow handle.

25. The safety device of claim 24, further comprising:
means for deterring leakage of such substance from the safety device.

26. The safety device of claim 25, wherein:
the leakage-deterring means comprise a sealing material applied to moving parts of the releasing and retracting means.

27. The safety device of claim 25, wherein:
the leakage-deterring means comprise an absorbent mass disposed within the hollow handle.

28. The safety device of claim 24, in further combination with:
such syringe.

29. The safety device of claim 23, for use with such a syringe that is a separate article and that has a standard-size front fitting for passage of liquids between the separate syringe and the patient's body;
the communication-establishing means comprise a standard-size rear fitting on the hollow handle for attachment of such separate syringe; and
the hollow needle has another end in communication with the interior of the hollow handle;
whereby said passage of substance between the separate syringe and the patient's body is by way of the rear fitting, the hollow handle, and the needle.

30. The safety device of claim 29, in further combination with:
such syringe.

31. The safety device of claim 23, in further combination with:
means for deterring leakage of such substance from the safety device.

32. The safety device of claim 31, wherein:
the leakage-deterring means comprise a sealing material applied to moving parts of the releasing and retracting means.

33. The safety device of claim 31, wherein:
the leakage-deterring means comprise an absorbent mass disposed within the hollow handle.

34. The safety device of claim 31, wherein:
the leakage-deterring means comprise a Teflon® sponge disposed within the hollow handle.

35. The safety device of claim 31, wherein the leakage-deterring means comprise:
a sealing material applied to moving parts of the releasing and retracting means; and
an absorbent mass disposed within the hollow handle.

36. The safety device of claim 31, in further combination with:
such syringe.

37. The safety device of claim 23, in further combination with:
such syringe.

38. The safety device of claim 23, wherein:

the trigger mechanism is actuable by one hand of a user of the device.

39. The safety device of claim 23, wherein:
the trigger mechanism includes a projection from the handle, adapted for manual actuation by a user of the device to release the block.

40. The safety device of claim 23, wherein:
a guideway is defined within the handle to guide the block rearward from the aperture.

41. The safety device of claim 23, wherein:
a stop is defined within the handle, opposite the aperture, for halting the motion of the block after actuation of the trigger mechanism;
whereby the block and needle are retained within the handle.

42. The safety device of claim 23, further comprising:
a stop element extending laterally from the block;
means for biasing the stop element outward from the block; and
a stop surface, defined within the handle, that engages the stop element to restrain the block from moving within the handle; and
wherein the handle has an external surface; and
the trigger mechanism includes a manually operable release member, accessible at or through the external surface of the handle, for forcing the laterally extending stop element inward against the action of the outward biasing means to release the block.

43. The safety device of claim 23, further comprising:
a stop element extending laterally within the handle;
means for biasing the laterally extending stop element inward from the handle; and
a stop surface, defined on the block, that engages the laterally extending stop element to restrain the block from moving within the handle; and
wherein the handle has an external surface; and
the trigger mechanism includes a manually operable release member, accessible at or through the external surface of the handle, for forcing the laterally extending stop element outward against the action of the inward biasing means to release the block.

44. The safety device of claim 23, further comprising:
stop elements respectively defined within the handle and on the block, for engaging each other over a limited range of angular positions of the block within the handle to restrain the block from retracting the needle; and
wherein the handle has an external surface; and
wherein the trigger mechanism includes a manually operable release member, accessible at or through the external surface of the handle, for forcibly rotating the block out of said range of angular positions to release the block.

* * * * *

UNITED STATES PATENT AND TRADEMARK OFFICE
CERTIFICATE OF CORRECTION

PATENT NO. : 4,900,307
DATED : February 13, 1990
INVENTOR(S) : John C. Kulli

It is certified that error appears in the above-identified patent and that said Letters Patent is hereby corrected as shown below:

Title page,
Item [*] Notice, should read:
-- This patent is subject to a terminal disclaimer. --

Signed and Sealed this

Fifth Day of July, 2005

JON W. DUDAS
*Director of the United States Patent and Trademark Office*